(12) United States Patent
Kameyama

(10) Patent No.: US 6,448,393 B1
(45) Date of Patent: Sep. 10, 2002

(54) PROCESS FOR PRODUCING 3-CEPHEM COMPOUNDS

(75) Inventor: Yutaka Kameyama, Tokushima (JP)

(73) Assignee: Otsuka Kagaku Kabushiki Kaisha, Osaka (JP)

( * ) Notice: Subject to any disclaimer, the term of this patent is extended or adjusted under 35 U.S.C. 154(b) by 0 days.

(21) Appl. No.: 09/529,530

(22) PCT Filed: Oct. 16, 1998

(86) PCT No.: PCT/JP98/04676

§ 371 (c)(1),
(2), (4) Date: Apr. 14, 2000

(87) PCT Pub. No.: WO99/20631

PCT Pub. Date: Apr. 29, 1999

(30) Foreign Application Priority Data

Oct. 17, 1997 (JP) ............................................. 9-303765

(51) Int. Cl.⁷ ...................... C07D 501/26; C07D 501/36
(52) U.S. Cl. ........................................ 540/226; 540/224
(58) Field of Search ................................. 540/215, 224, 540/226

(56) References Cited

U.S. PATENT DOCUMENTS

| 4,474,779 A | * 10/1984 | Nagano | 544/27 |
| 5,070,194 A | 12/1991 | Sasaoka et al. | 540/214 |
| 5,200,404 A | * 4/1993 | Jung | 514/206 |

FOREIGN PATENT DOCUMENTS

| EP | A-251299 | 1/1988 |
| JP | 61-263984 | 11/1986 |
| JP | 63022094 | 1/1988 |
| JP | 2-288884 | 11/1990 |
| WO | WO-1900900 | * 8/1986 |

* cited by examiner

Primary Examiner—Mark L. Berch
(74) Attorney, Agent, or Firm—Arent Fox Kintner Plotkin & Kahn

(57) ABSTRACT

3-Halogenomethylcephem compound of the formula (2) or its salt is obatined by deprotecting with phenol derivative a carboxylic acid protecting group at the 4-position of 7-amino-3-halogenomethylcephem compound of the formula (1) or its salt

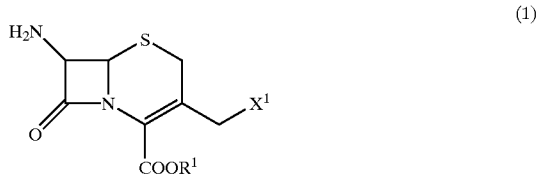

(1)

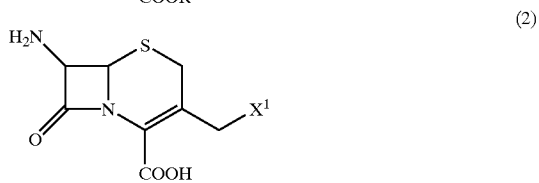

(2)

Further 3-thiomethylcephem compound of the formula (4) or its salt is prepared by reacting 3-halogenomethylcephem compound of the formula (2) or its salt with thiol compound or its salt of the formula (3)

$$R^2S-M$$

(3)

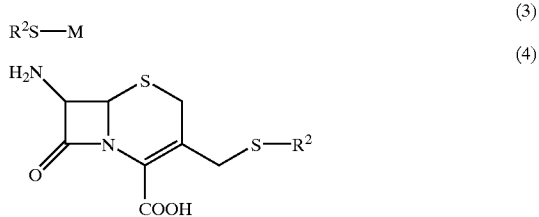

(4)

wherein $X^1$, $R^1$, $R^2$ and M are as defined in the specification.

4 Claims, No Drawings

PROCESS FOR PRODUCING 3-CEPHEM COMPOUNDS

TECHNICAL FIELD

The present invention relates to a process for preparing 3-halogenated methylcephem compound of high reactivity which can be used in place of 7-aminocephalosporanic acid (7-ACA) generally used as a conventional starting material. The invention also relates to a process for preparing 3-thiomethylcephem compound which is an important intermediate of various antibiotic substances.

3-Thiomethylcephem compounds prepared in the present invention are useful intermediates of antibiotic substances represented by cefazolin and ceftriaxone. These antibiotic substances are excellent antibacterial agents having a wide range antibacterial spectrum as disclosed in, for example, Handbook of Latest Antibiotics, 9th ed., Katsuji Sakai, P. 59 and P. 73.

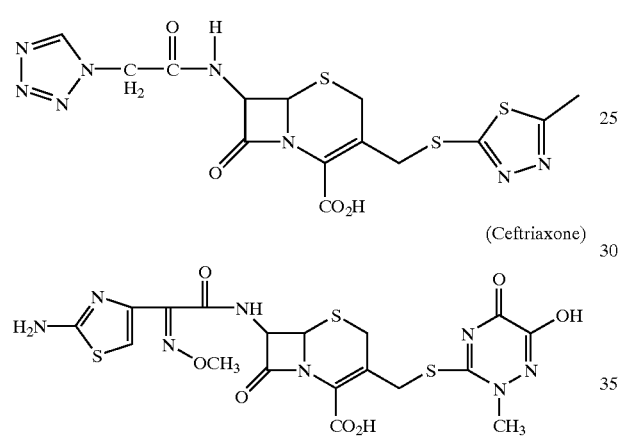

(Cefazolin)

(Ceftriaxone)

BACKGROUND ART

As a process for preparing 3-halogenated methylcephem compounds, there has been usually employed a process in which, by utilizing 7-aminocephalosporanic acid (7-ACA) generally used in preparing cephalosporanic antibiotic substances, amino group and carboxylic acid are protected with silyl group, and the acetoxy group is halogenated, followed by deprotection of the silyl protecting groups at the 7-position and 4-position. In this process, however, an expensive silyl reagent of not less than 2 equivalents is required, and a very expensive reagent such as trimethylsilyl iodide is needed in the conversion of acetoxy group into halogen atom. Since these reagents are highly sensitive to water, it is necessary to maintain the reaction system free from water. This process is therefore unsuitable industrially.

As a process for preparing 3-thiomethylcephem compounds, there has been usually employed a process in which 7-aminocephalosporanic acid (7-ACA) is directly reacted with thiol or its salt. This process, however, constrains the reaction at high temperatures, because the reactivity of acetoxy group is low. In this event, not only a decrease in reaction yield and an increase in by-product are unavoidable, but also isolation and purification operation is complicated. That is, this process is not always advantageous industrially. Accordingly, there has been a desire for a process for preparing 3-halogenomethylcephem compounds or 3-thiomethylcephem compounds, which is industrially feasible with ease, and is highly practical.

An object of the present invention is to establish an industrially feasible process for preparing 3-halogenomethylcephem compounds, and provide a process for preparing 3-thiomethylcephem compounds by using 3-halogenomethylcephem compound as a starting material.

DISCLOSURE OF THE INVENTION

The present invention provides a process for preparing 3-halogenomethylcephem compound of the formula (2) or its salt, comprising a carboxylic acid protecting group at the 4-position of 7-amino-3-halogenomethylcephem compound of the formula (1) or its salt is deprotected with phenol derivative

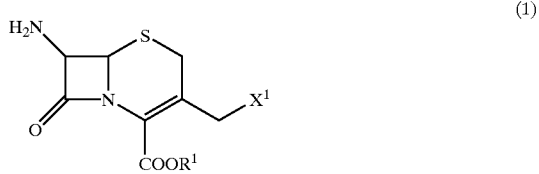

(1)

wherein $X^1$ is halogen atom; and $R^1$ is benzyl group which has on a phenyl ring an electron-donating group as a substituent, or diphenylmethyl group which may have an electron-donating group on a phenyl ring

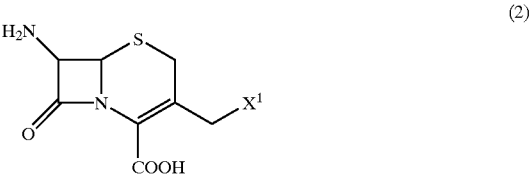

(2)

wherein $X^1$ is halogen atom.

The present invention also provides a process for preparing 3-thiomethylcephem compound of the formula (4) or its salt, comprising 3-halogenomethylcephem compound of the formula (2) or its salt is reacted with thiol compound or its salt of the formula (3)

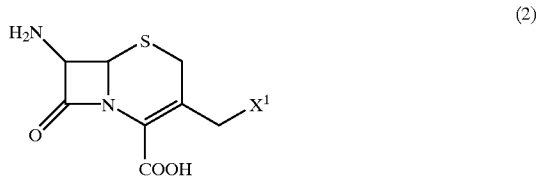

(2)

wherein $X^1$ is halogen atom

$R^2S—M$ (3)

wherein $R^2$ is nitrogen-containing aromatic heterocyclic group which may have a substituent; and M is hydrogen atom, alkali metal or alkaline earth metal

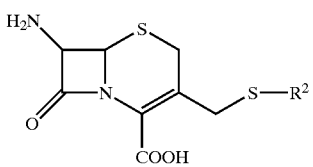

(4)

The present invention further provides a process for preparing 3-thiomethylcephem compound or its salt, comprising a carboxylic acid protecting group at the 4-position of 7-amino-3-halogenomethylcephem compound of the formula (1) is deprotected with phenol derivative and, without isolation, reacted with thiol compound or its salt of the formula (3), thereby obtaining 3-thiomethylcephem compound of the formula (4) or its salt.

The conventional process for preparing 3-thiomethylcephem compounds by employing 7-ACA as a starting material, suffers from the drawbacks of the low reaction yield and the formation of by-product, resulting in an unsatisfactory process. To establish an industrially feasible process, the inventors regarded that these drawbacks were due to the low reactivity of the acetoxy group at the C-3' position, and employed 3-halogenomethylcephem compounds which have at the C-3' position a halogen atom having a higher reactivity, as a starting material. However, any practical process for preparing these compounds were not known. Therefore, by utilizing a deprotection reaction in which phenol derivative is used for the carboxyl group at the 4-position of 7-amino-3-halogenomethylcephem compound, the inventors established an industrially feasible process for preparing 3-halogenomethylcephem compounds, as well as a process with which 3-thiomethylcephem compound is prepared from 7-amino-3-halogenomethylcephem compound at high purity and high yield.

The process of the invention enables to smoothly proceed the reaction at environmental temperature, minimize by-product, and facilitate the isolation and purification of a desired product. That is, this process has a higher industrial practicality than the conventional reaction using the 7-ACA as a starting material.

Also, the process of the invention enables to prepare 3-halogenomethylcephem compounds and 3-thiomethylcephem compounds at high purity and high yield, in such a manner as to be industrially feasible with ease.

Examples of the groups mentioned in the specification are as follows. Exemplary of the halogen atom are fluorine atom, chlorine atom, bromine atom and iodine atom. Examples of lower alkyl group are straight-chain or branched-chain $C_1$–$C_4$ alkyl groups such as methyl, ethyl, n-propyl, isopropyl, n-butyl, isobutyl, sec-butyl and tert-butyl. Exemplary of aryl group are phenyl and naphthyl.

Examples of electron-donating group substituted on the phenyl ring of benzyl group or diphenylmethyl group represented by $R^1$ are hydroxy; methyl, ethyl, tert-butyl and like lower alkyl groups; and methoxy, ethoxy and like lower alkoxy groups. The diphenylmethyl group includes a type of the group which is a substituted or unsubstituted phenyl group bonded in the molecule via methylene chain or hetero-atom. There are, for example, p-methoxybenzyl, diphenylmethyl, 3,4,5-trimethoxybenzyl, 3,5-dimethoxy-4-hydroxybenzyl, 2,4,6-trimethylbenzyl and ditolylmethyl.

Examples of nitrogen-containing aromatic heterocyclic group which may have a substituent represented by $R^2$ are triazolyl, triazinyl, thiadiazolyl, tetrazolyl and benzothiazolyl. Examples of substituent which can substitute for the heterocyclic group are lower alkyl group, sulfo lower alkyl group, carboxy lower alkyl group, amino lower alkyl group, lower alkyl substituted amino lower alkyl group and hydroxy lower alkyl group.

Examples of thio group represented by $R^2S$— are thio substituents among the known substituents at the 3-position of cephalosporin as described in USAN and the USP dictionary of drugs names. There are, for example, 1,2,3-triazol-4-ylthio, 5-methyl-1,3,4-thiadiazol-2-ylthio, 1-methyltetrazol-5-ylthio, 1-sulfomethyltetrazol-5-ylthio, 1-carboxymethyltetrazol-5-ylthio, 1-(2-dimethylaminoethyl)tetrazol-5-ylthio, 1,3,4-thiadiazol-5-ylthio, 1-(2-hydroxyethyl)tetrazol-5-ylthio, 3-methyl-1,3,4-triazine-5,6-dione-2-thio, and benzothiazol-2-thio.

Examples of alkali metal or alkaline earth metal represented by M are lithium, sodium, potassium, calcium and magnesium.

The 3-halogenomethylcephem compounds (1) used as a starting material in the invention can be easily prepared in the following manner that 7-phenylacetamide-3-chloromethylcephem-4-carboxylate prepared by a process as described in the literature of Torii et al., Tetrahedron Lett., 23, 2187 (1982), is subjected to deprotection of the 7-position amide side chain, by a process as described in RECENT ADVANCES IN THE CHEMISTRY OF β-Lactam Antiobiotics pp. 109–124, 1980 edited by G. I. Gregory.

In the present invention, the compounds (1) include the salt of the 7-position amino group. Examples of the salt are hydrohalogenic acid salt such as hydrochloride, hydrobromide and hydroiodide; sulfate; hydroperhalogenic acid salt such as perchlorate and periodate; and sulfonates such as p-toluenesulfonate.

Examples of the phenol derivative used in the present invention are phenol, m-cresol, o-cresol and p-cresol. Any other compound which has a phenolic hydroxyl group can be used. The amount of a phenol derivative used in the reaction as described is 1 to 1000 equivalents, preferably 5 to 100 equivalents, to the compound (1). In order to facilitate the reaction, acid can be used as required. Examples of the acid are mineral acids such as hydrochloric acid, sulfuric acid, nitric acid and phosphoric acid; and organic acids such as formic acid, acetic acid, propionic acid and trifluoroacetic acid. Any other one which is an acid substance can be used. The reaction temperature depends on the kind of the compound (1) and the kind of the phenol derivative, but it is usually 5 to 80° C., preferably 15 to 50° C. The reaction time depends on the kind of the compound (1), the kind of the phenol derivative and the reaction temperature, but it is usually terminated in 1 to 5 hours. If some material remains, the reaction time may be extended, which causes no problems.

In the present invention, 3-thiomethylcephem compound of the formula (4) or its salt is prepared by reacting 3-halogenomethylcephem compound of the formula (2) or its salt with thiol compound or its salt of the formula (3).

As exemplary of the salt of the compound (2), there are the salt of the 7-position amino group, and the salt of the 4-position carboxylic acid. Examples of the salt of the 7-position amino group are hydrohalogenic acid salt such as hydrochloride, hydrobromide and hydroiodide; sulfate; hydroperhalogenic acid salt such as perchlorate and periodate; and sulfonates such as p-toluenesulfonate. Examples of the salt of the 4-position carboxylic acid are alkali metal salts such as sodium and potassium; alkaline earth metal salts such as calcium; and aluminum salt. Also, salt can be formed from ion-exchange resin, together with the 7-position amino group or the 4-position carboxylic acid.

As thiol compound of the formula (3), an alkali metal salt or alkaline earth metal salt can be used, and thiol compound (when M is H) can also be used. In this case, the reaction may be conducted by the conjoint use of a variety of bases, depending on the reaction conditions.

Examples of bases used herein are basic ion-exchange resin; alkali metal hydroxides such as sodium hydroxide and potassium hydroxide; alkali metal carbonates such as sodium carbonate and potassium carbonate; alkali metal hydrogencarbonates such as sodium hydrogencarbonate and potassium hydrogencarbonate; ammonia; tertiary amines substituted by a lower alkyl group such as methyl, ethyl, propyl, isopropyl or t-butyl, and quaternary ammonium salt thereof. The amount of the base is usually 1 to 100 equivalents, preferably 1 to 30 equivalents, to the compound (2). The above-mentioned bases may be mixed together as required.

Examples of solvents are water, ketones such as acetone; ethers such as THF and dioxane; hydrocarbon halides such as methylene chloride and chloroform; nitrites such as acetonitrile, propionitrile, butyronitrile, isobutyronitrile and valeronitrile; and dimethyl sulfoxide. These can be used singly or in a mixture of at least two of them. Alternatively, it is possible to use a mixed solvent in which the above solvent is used mainly and other usual solvents are added thereto. As the usual solvents, there are, for example, lower alkyl esters of lower carboxylic acids such as methyl formate, ethyl formate, propyl formate, butyl formate, methyl acetate, ethyl acetate, propyl acetate, butyl acetate, methyl propionate and ethyl propionate; ethers such as diethyl ether, ethyl propyl ether, ethyl butyl ether, dipropyl ether, diisopropyl ether, dibutyl ether, methylcellosolve and dimethoxyethane; cyclic ethers such as tetrahydrofuran and dioxane; substituted or unsubstituted aromatic hydrocarbons such as benzene, toluene, xylene, chlorobenzene and anisole; hydrocarbons such as pentane, hexane, heptane and octane; cycloalkanes such as cyclopentane, cyclohexane, cycloheptane and cyclooctane; and halogenated hydrocarbons such as dichloromethane, chloroform, dichloroethane, trichloroethane, dibromoethane, propylene dichloride and carbon tetrachloride. Particularly preferred solvent are mixed solvents of which main solvent is water, dimethylformamide, 1-methyl-2-pyrrolidinone or dimethyl sulfoxide.

These solvents are used in an amount of about 0.5 to 200 liter, preferably about 1 to 50 liter, per 1 kg of the compound (2). The reaction is conducted in the range of −10 to 80° C., preferably 0 to 50° C.

In the present invention, 3-thiomethylcephem compound of the formula (4) or its salt can be obtained in the following manner that a carboxylic acid protecting group at the 4-position of 7-amino-3-halogenomethylcephem compound of the formula (1) is deprotected with phenol derivative and, without isolation, reacted with thiol compound or its salt of the formula (3). The deprotection and the reaction with a thiol compound or its salt, can be conducted in the same manner as described above.

The compound of the formula (4) can be obtained as an approximately pure product, by performing, after the reaction is terminated, the usual extraction or crystallization. It is, of course, possible to purify by any other method.

BEST MODE OF CARRYING OUT THE INVENTION

The present invention will be described in further detail by the following examples, a comparative example and a reference example.

Preparation of 3-halogenomethylcephem compounds

EXAMPLE 1

After weighing out 70 g of hydrochloride of a compound of the formula (1) ($R^1$=CHPh$_2$, $X^1$=Cl) (1a), 210 ml of phenol was added thereto and stirred at a temperature of 45 to 50° C., for 30 minutes. Separately, 1100 ml of diisopropyl ether was weighed out to a 2 L four-necked flask, and fully stirred at room temperature. When the reaction was terminated, the phenol solution was gradually dropped in the diisopropyl ether, thereby depositing a compound in powder form. This was filtered under reduced pressure, and dried under reduced pressure, to give 44 g (yield: 99%) of the hydrochloride of a compound 2a ($X^1$=Cl).

$^1$H NMR (300 MHz, DMSO-d$_6$) δ3.65 (d, J=18 Hz, 1H), 3.74(d, J=18 Hz, 1H), 4.54(d, J=11 Hz, 1H), 4.61(d, J=11 Hz, 1H), 5.17(d, J=5 Hz, 1H), 5.23(d, J=5 Hz, 1H).

EXAMPLE 2

The reaction was conducted in the same manner as in Example 1 except that the hydrochloride of a compound of the formula (1) ($R^1$=p-methoxybenzyl, $X^1$=Cl) (1b) was used in place of the hydrochloride of the compound 1a, to give 43 g (yield: 97%) of the hydrochloride of a desired 3-halogenomethylcephem compound (2a). The obtained hydrochloride of the compound (2a) was identical with that of Example 1 in $^1$H-NMR.

EXAMPLE 3

The reaction was conducted in the same manner as in Example 1 except that m-cresol was used in place of phenol, and the reaction was continued for 4 hours at room temperature, to give 44 g (yield: 99%) of the hydrochloride of a desired 3-halogenomethylcephem compound (2a). The obtained hydrochloride of the compound (2a) was identical with that of Example 1 in $^1$H-NMR.

EXAMPLE 4

The reaction was conducted in the same manner as in Example 1 except that a compound 1b was used in place of the compound 1a, m-cresol was used in place of phenol, and the reaction was continued for 3 hours at room temperature, to give 44 g (yield: 99%) of the hydrochloride of a desired 3-halogenomethylcephem compound (2a). The obtained hydrochloride of the compound (2a) was identical with that of Example 1 in $^1$H-NMR.

Preparation of 3-thiomethylcephem compounds

EXAMPLE 5

5-Methyl-2-mercapto-1,3,4-thiadiazole (730 mg) and 930 mg of sodium hydrogencarbonate were weighed out to a 100-ml four-necked flask, and dissolved by adding 20 ml of water. To this mixture, 1 g of the hydrochloride of compound (2a) was added to undergo a reaction at room temperature for 7 hours. When the reaction was terminated, the pH of the reaction mixture was adjusted to 1, by adding a concentrated hydrochloric acid. Then, an insoluble substance was filtered to obtain a filtrate. By using a 5% aqueous ammonia, the pH of the filtrate was adjusted to 3.8 at 3° C., thereby depositing crystal. The obtained crystal was filtered and dried under reduced pressure, to give 1.1 g (yield: 90%) of a 3-thiomethylcephem compound 4a ($R^2$S=5-methyl-1,3,4-thiadiazol-2-ylthio).

$^1$H NMR (300 MHz, D$_2$O) δ2.57 (s, 3H), 3.24(d, J=18 Hz, 1H), 3.64(d, J=18 Hz, 1H), 3.75(d, J=14 Hz, 1H), 4.33(d, J=14 Hz, 1H), 4.86(d, J=5 Hz, 1H), 5.26(d, J=5 Hz, 1H).

EXAMPLES 6 to 13

The reaction was conducted in the same manner as in Example 5 except that the solvent was changed as follows. Table 1 gives the results.

TABLE 1

| Example | solvent | | | | yield (%) |
|---|---|---|---|---|---|
| 6 | DMF | 10 ml | water | 10 ml | 87 |
| 7 | DMSO | 10 ml | water | 10 ml | 85 |
| 8 | NMP | 10 ml | water | 10 ml | 88 |
| 9 | THF | 10 ml | water | 10 ml | 79 |
| 10 | dioxane | 10 ml | water | 10 ml | 80 |
| 11 | DMF | 20 ml | | | 75 |
| 12 | NMP | 20 ml | | | 77 |
| 13 | DMSO | 20 ml | | | 70 |

NMP designates N-methyl-2-pyrrolidone, DMF designates N,N-dimethylformamide, DMSO designates dimethylsulfoxide, and THF designates tetrahydrofuran.

EXAMPLE 14

The reaction was conducted in the same manner as in Example 5 except that 640 mg of 5-mercapto-1-methyltetrazole was used in place of 730 mg of 5-methyl-2-mercapto-1,3,4-thiadiazole, to give 1.0 g (yield: 88%) of 3-thiomethylcephem compound 4b ($R^2S$=1-methyltetrazol-5-ylthio).

$^1$H NMR (300 MHz, $D_2O$) δ3.30 (d, J=18 Hz, 1H), 3.64(d, J=18 Hz, 1H), 3.85(d, J=14 Hz, 1H), 3.89(s, 3H), 4.17(d, J=14 Hz, 1H), 4.88(d, J=5 Hz, 1H), 5.26(d, J=5 Hz, 1H).

EXAMPLE 15

A 860 mg-quantity of $R^2SH$ ($R^2$: as defined below) and 930 mg of sodium hydrogencarbonate were weighed out to a 100-ml four-necked flask, and dissolved by adding 20 ml of water. To this mixture, 1 g of hydrochloride of the compound 2a ($X^2$=Cl) was added to undergo a reaction at room temperature for 25 hours. As the reaction proceeded, crystal was deposited. The obtained crystal was filtered and dried under reduced pressure, to give 1.2 g (yield: 93%) of a 3-thiomethylcephem compound 4c ($R^2$: as defined below).

$^1$H NMR (300 MHz, DMSO-$d_6$) δ3.18 (d, J=14 Hz, 1H), 3.64(s, 3H), 3.78(d, J=12 Hz, 1H), 3.88(d, J=12 Hz, 1H), 4.58(d, J=4 Hz, 1H), 4.61(s, 1H), 4.70(d, J=14 Hz, 1H), 5.30(d, J=4 Hz, 1H).

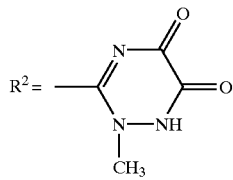

EXAMPLE 16

A 300 mg-quantity of the hydrochloride of a compound of the formula (1) ($R^1$=$CH_2C_6H_4OCH_3$-p, $X^1$=Cl) (1b) was weighed out, and 1 ml of phenol was added thereto and stirred at a temperature of 45 to 50° C. for 1 hour. To this mixture, 4 ml of ethyl acetate was added to obtain a suspension. Then, 4 ml of aqueous solution containing 147 mg of $R^2SH$ (5-methyl-2-mercapto-1,3,4-thiadiazole) prepared separately, and 197 mg of sodium hydrogencarbonate, were added to the suspension and stirred at room temperature for 27.5 hours. Thereby, a desired compound was deposited, which was then filtered, washed with 5 ml of acetone, and dried under reduced pressure, to give a desired compound 4a (245 mg, yield 96%). The obtained compound 4a was identical with that of Example 5 in $^1$H-NMR spectrum.

EXAMPLE 17

After weighing out 1 g of the hydrochloride of a compound of the formula (1) ($R^1$=$CH_2C_6H_4OCH_3$-p, $X^1$=Cl) (1b), 3 ml of phenol was added thereto and stirred at a temperature of 45 to 50° C. for 1 hour. To this mixture, 10 ml of ethyl acetate was added to obtain a suspension. Then, 10 ml of aqueous solution containing 603 mg of $R^2SH$ (the same thiol compound as Example 15) prepared separately, and 656 mg of sodium hydrogencarbonate, were added to the suspension and stirred at room temperature for 19 hours. Thereby, a desired compound was deposited, which was then filtered, washed with 10 ml of acetone, and dried under reduced pressure, to give a desired compound 4c (701 mg, yield 99%). The obtained compound 4c was identical with that of Example 15 in $^1$H-NMR spectrum.

COMPARATIVE EXAMPLE 1

The reaction was conducted in the same manner as in Example 15 except that 7-ACA was used as a starting material. As a result, the reaction hardly proceeded. In this reaction, when the reaction temperature was raised to 70° C., the reaction was proceeded. However, the yield was low, namely, 68%.

REFERENCE EXAMPLE 1

The following is an example in which cefazolin was prepared by using the compound 4a obtained in Example 5.

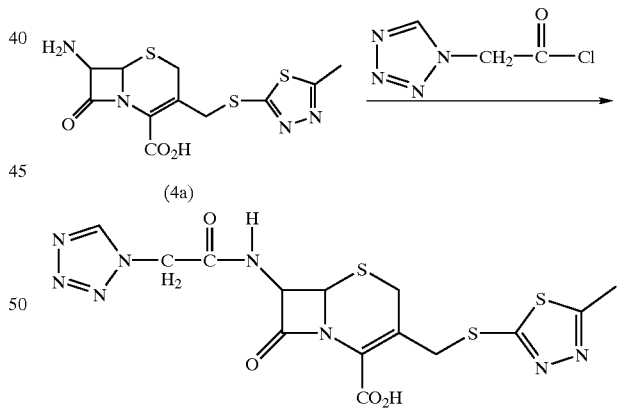

1) Preparation of a mixed acid anhydride:

Into a 100-ml four-necked flask were poured 3.72 g of tetrazole acetate and 40 ml of methylene chloride. To this methylene chloride solution, 2.94 g of triethylamine was added and cooled to −10° C. Below −10° C., 3.32 g of pivalic acid chloride was added. The temperature of the reaction mixture was adjusted to 0° C., and aged for 1 hour at 0° C.

2) Preparation of a solution of methylene chloride of the compound (4):

Into a 100-ml four-necked flask were poured 4.3 g of diisopropylamine and 30 ml of methylene chloride. To this methylene chloride solution, the compound 4a (2.94 g) was added, dissolved, and cooled to below −20° C.

3) Cefazolin Forming Reaction:

To the prepared mixed acid anhydride solution, the solution of the compound 4a in methylene chloride was dropped at a temperature below −20° C., for 20 to 30 minutes. After stopping cooling, the mixture was stirred at room temperature for 30 minutes. Upon confirming the completion of the reaction, 60 ml of water was added to extract cefazolin. In a similar manner, 40 ml of water was added to a methylene chloride layer, and cefazolin was extracted with water. The pH of the combined solution of the two cefazolin extracts was adjusted to 4.5. To the resulting solution, 30 ml of methylene chloride was added and the cefazolin extract was washed and then separated. Then, 1.5 g of activated charcoal was added thereto and stirred for 15 minutes, to filter the activated charcoal. The pH of the filtrate was adjusted to 2, by adding a 3N-hydrochloric acid solution, thereby depositing crystal. The obtained crystal was aged below 5° C. for 1 hour. Thereafter, cefazolin crystal was filtered, washed with 20 ml of cold water, and dried under reduced pressure, to give 5.92 g (yield: 90%) of the cefazolin crystal.

INDUSTRIAL APPLICABILITY

The present invention establishes an industrially feasible process for preparing 3-halogenomethylcephem compounds, and provides a process for preparing 3-thiomethylcephem compounds which are excellent intermediates of antibacterial agents having a wide range antibacterial spectrum, such as cefazolin and ceftriaxone.

What is claimed is:

1. A process for preparing a 3-thiomethylcephem compound of formula (4) or its salt, comprising:

preparing a compound of formula (2), or its salt by deprotecting a 7-amino-3-halogenomethylcephem compound of formula (1) or its salt with a compound having a phenolic hydroxyl group,

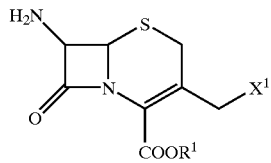 (1)

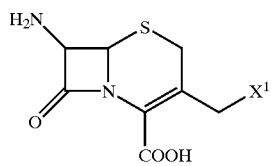 (2)

wherein $X^1$ is a halogen atom; and $R^1$ is a protective group which is a benzyl group which has on a phenyl ring an electron-donating group as a substituent, or diphenylmethyl group which may have an electron-donating group on a phenyl ring;

reacting the deprotected compound of formula (2) or its salt with a thiol compound or its salt of formula (3) to obtain a compound of formula (4),

 (3)

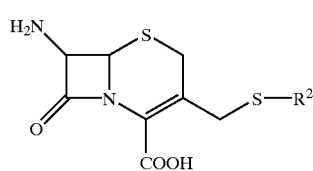 (4)

wherein $R^2$ is a nitrogen-containing aromatic heterocyclic group containing one or two aromatic rings which may have a substituent; and M is hydrogen atom, alkali metal or alkaline earth metal.

2. A process for preparing a 3-thiomethylcephem compound of formula (4) or its salt, comprising:

preparing a compound of formula (2), or its salt by deprotecting a 7-amino-3-halogenomethylcephem compound of formula (1) or its salt with a compound having a phenolic hydroxyl group,

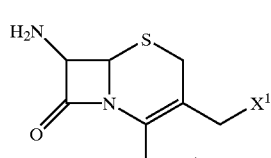 (1)

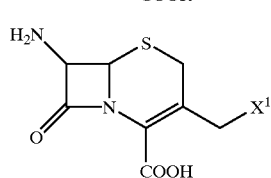 (2)

wherein $X^1$ is a halogen atom; and $R^1$ is a protective group which is a benzyl group which has on a phenyl ring an electron-donating group as a substituent, or diphenylmethyl group which may have an electron-donating group on a phenyl ring;

reacting the deprotected compound of formula (2) or its salt with a thiol compound or its salt of formula (3) to obtain a compound of formula (4), $R^2S—M$ (3)

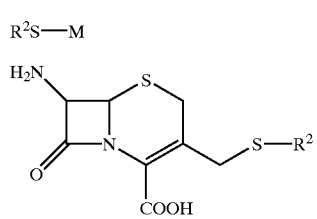 (4)

wherein $R^2$ is selected from the group consisting of triazolyl, triazinyl, thiadiazolyl, tetrazolyl and benzothiazolyl.

3. A process for preparing a 3-thiomethylcephem compound of formula (4) or its salt, comprising:

preparing a compound of formula (2), or its salt by deprotecting a 7-amino-3-halogenomethylcephem compound of formula (1) or its salt with a compound having a phenolic hydroxyl group,

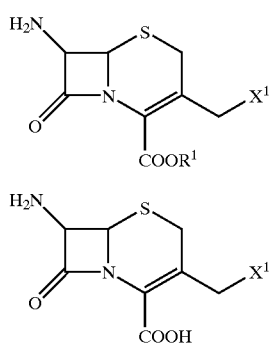
(1)

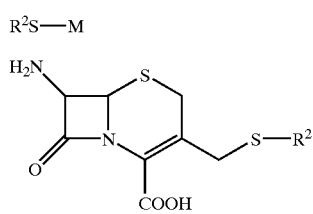
(2)

wherein X¹ is a halogen atom; and R¹ is a protective group which is a benzyl group which has on a phenyl ring an electron-donating group as a substituent, or diphenylmethyl group which may have an electron-donating group on a phenyl ring;

reacting the deprotected compound of formula (2) or its salt with a thiol compound or its salt of formula (3) to obtain a compound of formula (4), $$R^2S-M \quad (3)$$

(4)

wherein $R^2$ is a nitrogen-containing aromatic heterocyclic group containing one or two aromatic rings which may have a substituent, wherein the substituent is selected from the group consisting of lower alkyl, sulfo lower alkyl, carboxy lower alkyl, amino lower alkyl, lower alkyl substituted amino lower alkyl and hydroxy lower alkyl groups; and M is hydrogen atom, alkali metal or alkaline earth metal.

4. A process for preparing a 3-thiomethylcephem compound of formula (4) or its salt, comprising:

preparing a compound of formula (2), or its salt by deprotecting a 7-amino-3-halogenomethylcephem compound of formula (1) or its salt with a compound having a phenolic hydroxyl group,

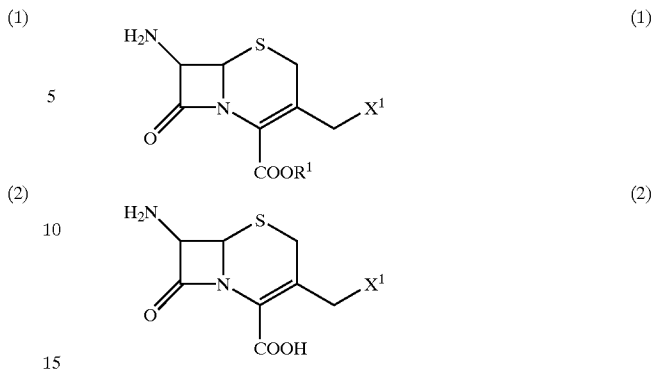
(1)

(2)

wherein X¹ is a halogen atom; and R¹ is a protective group which is a benzyl group which has on a phenyl ring an electron-donating group as a substituent, or diphenylmethyl group which may have an electron-donating group on a phenyl ring;

reacting the deprotected compound of formula (2) or its salt with a thiol compound or its salt of formula (3) to obtain a compound of formula (4), $$R^2S-M \quad (3)$$

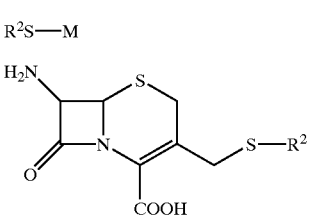
(4)

wherein $R^2$ is a nitrogen-containing aromatic heterocyclic group containing one or two aromatic rings which may have a substituent; and M is hydrogen atom, alkali metal or alkaline earth metal, wherein the thiol compound represented by $R^2S-$ is selected from the group consisting of 1,2,3-triazol-4-ylthio; 5-methyl-1,3,4-thiadiazol-2-ylthio; 1-methyltetrazol-5-ylthio; 1-sulfomethyltetrazol-5-ylthio; 1-carboxymethyltetrazol-5-ylthio; 1-(2-dimethylaminoethyl)tetrazol-5-ylthio, 1,3,4-thiadiazol-5-ylthio, 1-(2-hydroxyethyl)tetrazol-5-ylthio; 3-methyl-1,3,4-triazine-5,6-dione-2-thio and benzothiazol-2-thio.

* * * * *